US00PP32931P2

(12) United States Plant Patent
Pineau

(10) Patent No.: US PP32,931 P2
(45) Date of Patent: Mar. 30, 2021

(54) ***CAMPSIS* PLANT NAMED 'MINCAMJA3'**

(50) Latin Name: ***Campsis* x *tagliabuana***
Varietal Denomination: Mincamja3

(71) Applicant: Hortival Diffusion SAS, Beaufort en Anjou (FR)

(72) Inventor: Patrick Pineau, Saint Mathurin sur Loire (FR)

(73) Assignee: HORTIVAL DIFFUSION SAS, Beaufort en Anjou (FR)

( * ) Notice: Subject to any disclaimer, the term of this patent is extended or adjusted under 35 U.S.C. 154(b) by 0 days.

(21) Appl. No.: 16/602,397

(22) Filed: Sep. 30, 2019

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

(56) References Cited

U.S. PATENT DOCUMENTS

PP13,139 P2 10/2002 Kuijf

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of *Campsis* plant, herein referred to by its cultivar name, 'Mincamja3', is provided. The new variety displays golden yellow colored flowers with red stripes inside. The foliage of the new variety is medium green colored. The vegetation is moderately vigorous and the growth habit is climbing.

3 Drawing Sheets

Botanical/commercial classification:
Latin name of genus and species of plant claimed: *Campsis* x *tagliabuana*.
Variety denomination 'Mincamja3'.

BACKGROUND OF THE INVENTION

The present invention relates to a new and distinct cultivar of *Campsis* plant botanically known as *Campsis* x *tagliabuana* and hereinafter referred to by the cultivar name 'Mincamja3'.

The new cultivar originated in a controlled breeding program in La Menitre, Maine et Loire, France during July 2005. The objective of the breeding program was the development of a series of *Campsis* cultivars with big flower size and yellow flowers.

The new *Campsis* cultivar is the result of cross-pollination. The female parent (i.e., seed parent) of the new cultivar is an unnamed breeder seedling, characterized by its large peach-reddish colored flowers, medium green-colored foliage, and a vigorous climbing growth habit. The male parent (i.e., pollen parent) of the new cultivar is 'Kudian' (U.S. Plant Pat. No. 13,139) characterized by its orange-colored flowers, medium green-colored foliage, and moderately climbing habit. The parentage can be summarized as follows:

unnamed breeder seedling x 'Kudian'

The new cultivar was discovered and selected as a single flowering plant within the progeny of the above stated cross-pollination during October 2009 in a controlled environment in La Menitre, Maine et Loire, France.

Asexual reproduction of the new cultivar by grafting since February 2010 in La Menitre, Maine et Loire, France has demonstrated that the new cultivar reproduces true to type with all of the characteristics, as herein described, firmly fixed and retained through successive generations of such asexual propagation.

SUMMARY OF THE INVENTION

The new cultivar of the present invention possesses the following combination of characteristics, which have been repeatedly observed and can be used to distinguish 'Mincamja3' as a new and distinct cultivar of *Campsis* plant:

(a) forms golden yellow colored flowers with red stripes inside,
(b) exhibits medium green colored foliage, and
(c) forms moderately vigorous, climbing growth habit.

The new variety can be readily distinguished from its ancestors. More specifically, the female parent produces peach-reddish colored flowers, whereas the new variety produces golden yellow colored flowers with red stripes inside. Additionally, 'Kudian' (i.e., pollen parent) produces orange colored flowers, whereas the new variety produces golden yellow colored flowers with red stripes inside. Moreover, the new variety can be readily distinguished from non-parental related similar varieties. Of the many commercially available *Campsis* cultivars, the most similar in comparison to the new cultivar is 'Flava' (non-patented). However, plants of the new cultivar differ from plants of 'Flava' in at least the following characteristics:

1. Plants of the new cultivar have a brighter yellow colored flower with the presence of red stripes inside compared to plants of 'Flava'; and 2. Plants of the new cultivar have lighter green colored foliage compared to plants of 'Flava'.

BRIEF DESCRIPTION OF THE PHOTOGRAPH

The accompanying photographs show, as nearly true as it is reasonably possible to make the same in color illustrations of this type, typical specimen of the new variety. The illustrated plants of the new variety were approximately eight years old and were growing in the ground in La Menitre, Maine et Loire, France.

DETAILED BOTANICAL DESCRIPTION

Figure 1:
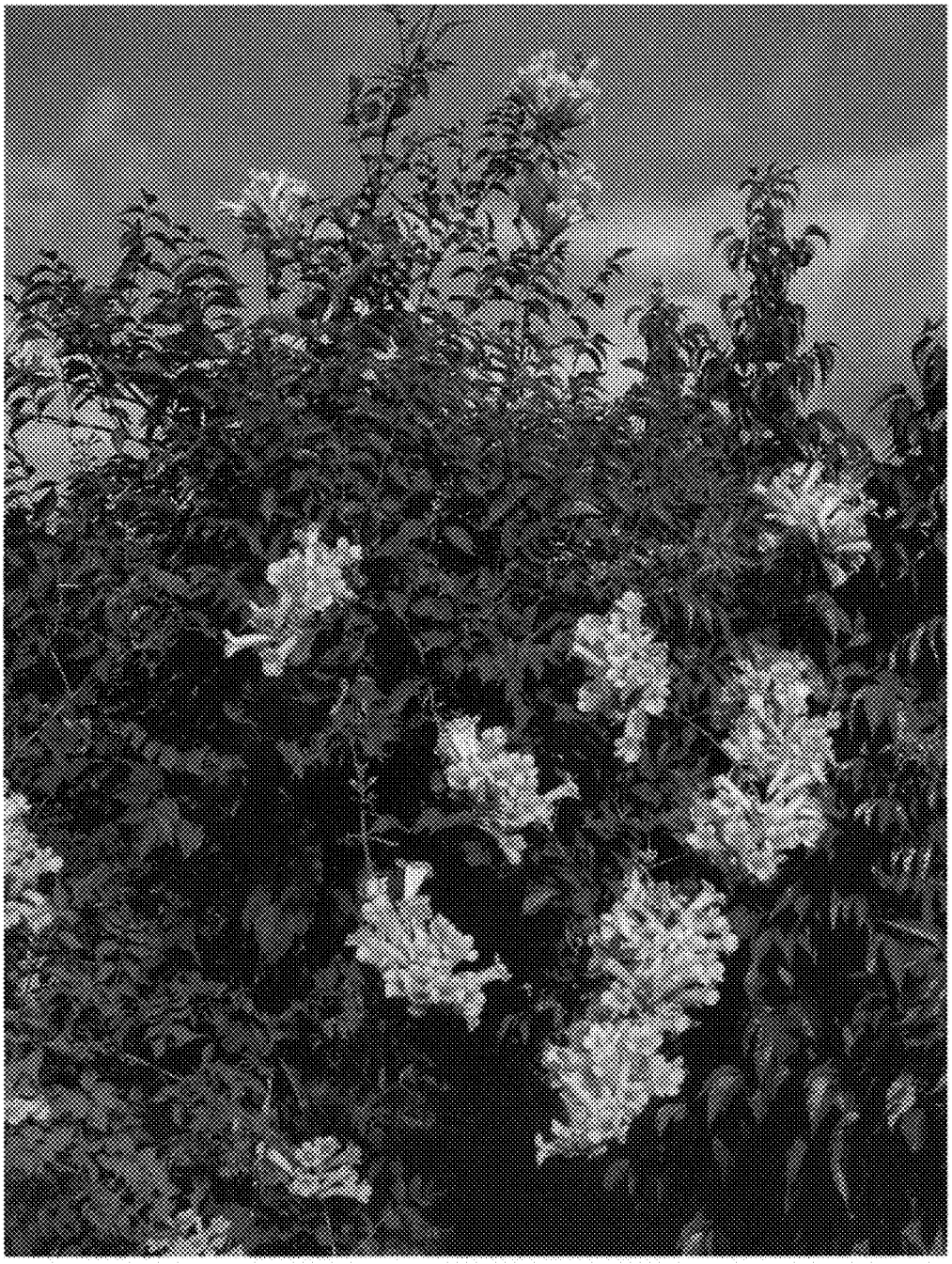
FIG. 1 illustrates a side view of the overall growth of a plant specimen and the flowering habit.
Figure 2:
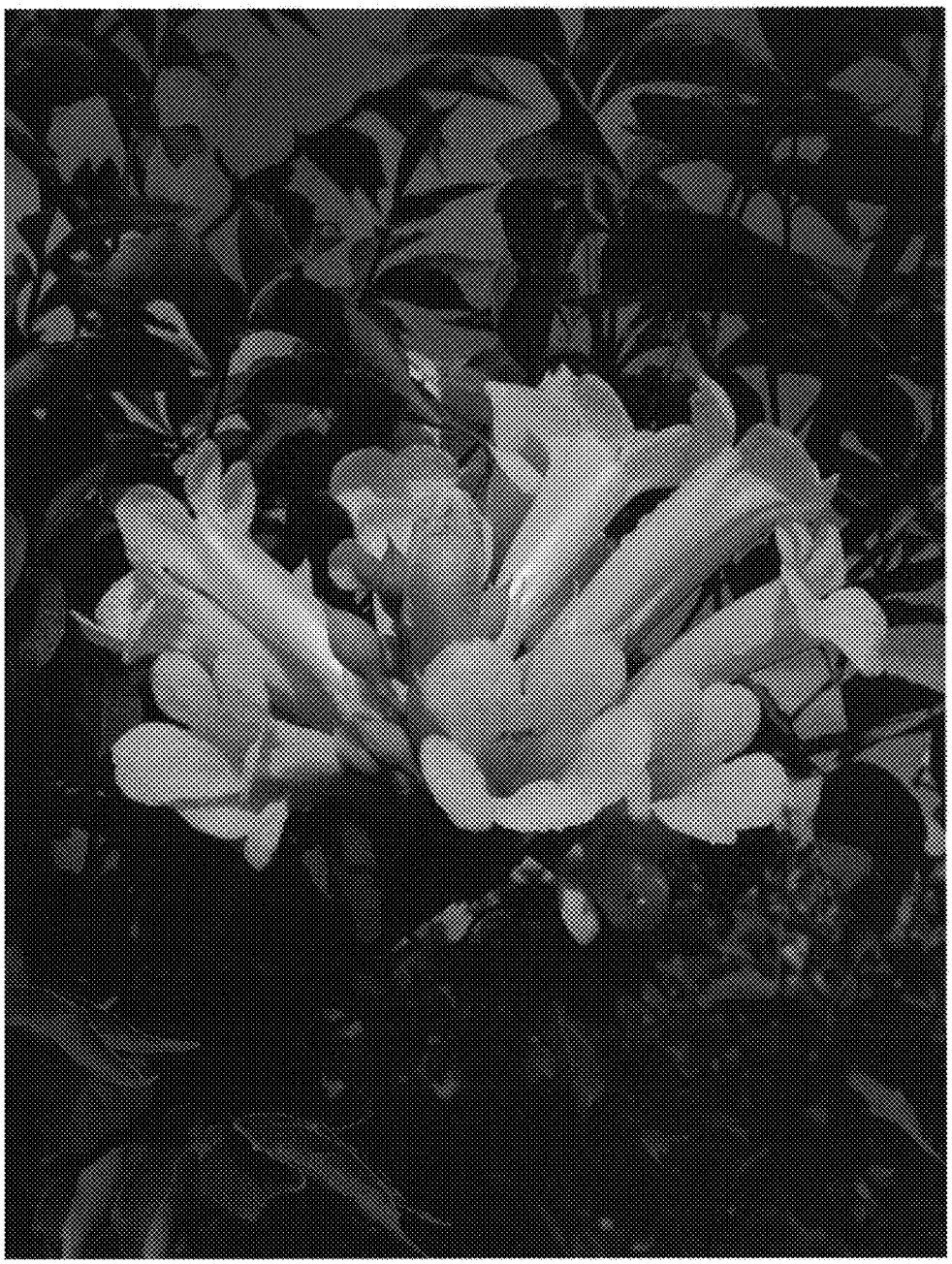
FIG. 2 illustrates an inflorescence specimen.
Figure 3:
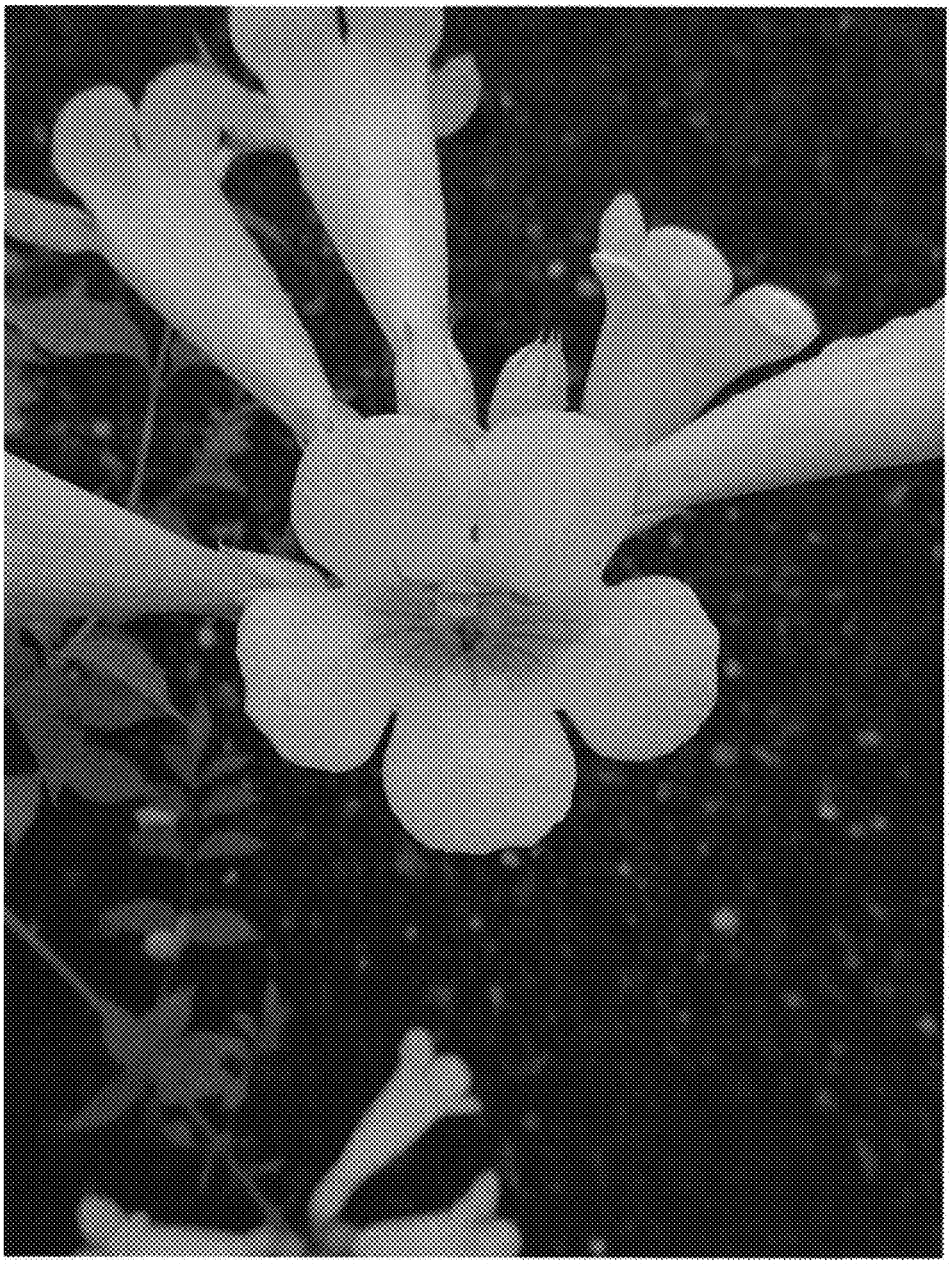
FIG. 3 illustrates a close-up view of a flower specimen.

The chart used in the identification of colors described herein is that of The Royal Horticultural Society (R.H.S. Colour Chart, London, England, 2015 edition), except where general color terms of ordinary significance are used. The terminology which precedes reference to the chart has been added to indicate the corresponding color in more common terms. The color values were determined in July 2020 under natural light conditions in Cochranville, Pa. The following descriptions and measurements describe plants grown in seven-gallon containers for approximately three years in an outdoor nursery in Cochranville, Pa.

Botanical classification: *Campsis* x *tagliabuana* cultivar Mincamja3.

Propagation:

*Type*.—Grafting.

*Root description*.—Fibrous.

*Rooting habit*.—Freely branching.

Plant:

*Commercial crop time*.—Approximately 12-15 months to finish in a 3-gallon container.

*Growth habit and general appearance*.—Moderately vigorous, climbing growth habit.

*Size*.—Height from soil level to top of plant plane: Approximately 90.0 cm. — Width: Approximately 110.0 cm.

*Branching habit*.—Freely branching. — Quantity of main branches per plant: Approximately 4. — Quantity of secondary branches per plant: Approximately 7 to 8.

*Branch*.—Strength: Strong, somewhat flexible, becomes woody with age. — Length of main branches: Approximately 90.0 cm. — Diameter of main branches: Approximately 1.0 cm. — Length of secondary branches: Approximately 30.0 cm. — Diameter of secondary branches: Approximately 5.0 mm. — Length of central internode: Approximately 6.0 cm. — Color of young stems: commonly near Greyed-Orange Group 177A. — Color of mature stems: commonly a blend of near Grey-Brown Group N199D and near Brown Group N200C. — Texture of young stems: Glabrous. — Texture of mature stems: Woody.

Foliage:

*General description*.—Quantity of leaves per branch: Approximately 13. — Quantity of leaves per branched lateral stem: Approximately 8. — Fragrance: None detected. — Type: Odd-Pinnate. — Arrangement: Opposite. — Durability to stress: Moderate to high.

*Leaves*.—Aspect: Primarily perpendicular to stem. — Length of mature leaf: Approximately 13.0 cm. — Width of mature leaf: Approximately 8.0 cm.

*Leaflets*.—Shape: Lanceolate to oblanceolate. — Margin: Serrulate. — Apex: Acute. — Base: Attenuate. — Venation pattern: Pinnate, reticulate. — Length: Approximately 4.0 cm. — Width: Approximately 1.8 cm. — Texture of upper surface: Glabrous. — Texture of lower surface: Glabrous to slightly pubescent. — Color of upper surface of mature foliage: commonly near Yellow-Green Group 146A with indistinguishable venation. — Color of lower surface of mature foliage: commonly near Yellow-Green Group 146B with venation of near Yellow-Green Group 146D.

*Petiole*.—Shape: Rounded, slightly flattened on upper surface. — Length: Approximately 7.0 cm. — Width: Approximately 3.0 mm. — Texture: Glabrous. — Color: commonly near Yellow-Green Group 144A.

*Petiolule*.—Shape: Curving upwards. — Length: Approximately 8.0 mm. — Width: Approximately 2.0 mm. — Texture: Glabrous. — Color: commonly near Yellow-Green Group 144A.

*Rachis*.—Shape: Rounded, slightly flattened on upper surface. — Length: Approximately 18.0 cm. — Width: Approximately 3.0 mm. — Texture: Glabrous. — Color: commonly near Yellow-Green Group 144A.

Flowering description:

*Flowering habit*.—freely flowering under outdoor growing conditions with substantially continuous blooming from mid-summer through early fall.

*Lastingness of individual flower*.—Approximately 5 to 7 days.

Inflorescence description:

*General description*.—Type: Terminal cluster of single flowers, blooms on current year's growth. — Quantity of open inflorescences per plant: Approximately 20. — Fragrance: None noticeable. — Depth or height of inflorescence: Approximately 13.0 cm. — Width: Approximately 13.0 cm.

Flower:

*Type*.—Tubular.

*Bud just before opening*.—Shape: Elliptic. — Length: Approximately 3.0 cm. — Diameter: Approximately 1.5 cm. — Texture: Glabrous. — Color: commonly near Yellow-Orange Group 20A.

*Petals*.—Shape: Flabellate with lobes rounded. — Margin: Entire to slightly notched and wavy. — Base: Fused. Apex: Rounded.

*Corolla tube*.—Length: Approximately 6.0 cm. — Width: Approximately 2.0 cm. — Diameter of throat opening: Approximately 1.5 cm. — Texture of inner surface: Glabrous. — Texture of outer surface: Glabrous. — Color of upper surface when first and fully open: commonly near Yellow-Orange Group 21A with parallel striping of near Red Group 47A. — Color of lower surface when first and fully open: commonly near Yellow-Orange Group 23B.

*Sepals*.—Quantity per flower: 4, fused at base. — Apex: Acute. — Margin of free portion: Entire. —

Length: Approximately 2.5 cm. — Width of free portion: 5.0 mm. — Texture of inner and outer surfaces: Glabrous. — Color of inner surface: Closest to Yellow Group 5B. — Color of outer surface: Closest to Yellow-Orange Group 16B.

*Pedicels*.—Strength: Strong. — Length: Approximately 1.0 cm. — Diameter: Approximately 3.0 mm. — Texture: Glabrous. — Color: commonly near Yellow-Green Group 144A.

*Peduncle*.—Strength: Strong. — Length: Approximately 5.0 cm. — Diameter: Approximately 4.0 mm. — Texture: Glabrous. — Color: commonly near Yellow-Green Group 144A.

Reproductive organs:

*Androecium*.—Stamen quantity: 4 per flower, attached to the corolla at the base. — Filament Length: 3.5 cm. — Filament Color: commonly near Yellow Group 8C. — Anther shape: Divergent. — Anther length: Approximately 5.0 mm. — Anther color: commonly near Yellow-Orange Group 22C.

*Gynoecium*.—Pistil quantity: 1 per flower. — Pistil length: Approximately 4.5 cm. — Stigma shape: Flattened petaloid. — Stigma length: Approximately 5.0 mm. — Stigma color: Closest to Yellow-Green Group 145A. — Style length: Approximately 3.5 cm. — Style color: Closest to Yellow-Green Group 145B. — Ovary length: Approximately 5.0 mm. — Ovary color: Closest to Yellow-Green Group 145C.

Development:

*Seed and fruit production*.—Neither seed nor fruit production has been observed.

*USDA hardiness*.—Zone 5-9.

*Disease and pest resistance*.—Resistance to pathogens and pests common to *Campsis* has not been observed.

The new cultivar has not been observed under all possible environmental conditions to date. Accordingly, it is possible that the phenotype may vary somewhat with variations in the environment, such as temperature, light intensity, and day length, without, however, any variance in genotype.

I claim:

1. A new and distinct cultivar of *Campsis* plant characterized by the following combination of characteristics:

(a) forms golden yellow colored flowers with red stripes inside, (b) exhibits medium green colored foliage, and (c) forms moderately vigorous, climbing growth habit; substantially as herein shown and described.

* * * * *